US010874369B2

(12) United States Patent
Lalena

(10) Patent No.: US 10,874,369 B2
(45) Date of Patent: Dec. 29, 2020

(54) GEOMETRIC CALIBRATION IN A CONE BEAM COMPUTED TOMOGRAPHY SYSTEM

(71) Applicant: CARESTREAM HEALTH, INC., Rochester, NY (US)

(72) Inventor: Michael C. Lalena, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 16/344,384

(22) PCT Filed: Nov. 1, 2017

(86) PCT No.: PCT/US2017/059429
§ 371 (c)(1),
(2) Date: Apr. 24, 2019

(87) PCT Pub. No.: WO2018/085316
PCT Pub. Date: May 11, 2018

(65) Prior Publication Data
US 2019/0254617 A1    Aug. 22, 2019

Related U.S. Application Data

(60) Provisional application No. 62/416,178, filed on Nov. 2, 2016.

(51) Int. Cl.
*A61B 6/00*     (2006.01)
*A61B 90/00*    (2016.01)
(Continued)

(52) U.S. Cl.
CPC .............. *A61B 6/5205* (2013.01); *A61B 6/03* (2013.01); *A61B 6/032* (2013.01); *A61B 6/04* (2013.01); *A61B 6/14* (2013.01); *A61B 6/4085* (2013.01); *A61B 6/4405* (2013.01); *A61B 6/501* (2013.01); *A61B 6/5252* (2013.01); *A61B 6/582* (2013.01);
(Continued)

(58) Field of Classification Search
CPC ........... A61B 6/032; A61B 6/03; A61B 6/584; A61B 6/582; A61B 6/585; A61B 6/5205; A61B 6/5252; A61B 6/501; A61B 6/4085; A61B 90/39; A61B 6/588; G06T 11/005
See application file for complete search history.

(56) References Cited

U.S. PATENT DOCUMENTS 6,379,043 B1    4/2002  Zylka et al.
9,597,044 B2 *  3/2017  Yorkston ................ A61B 6/032
(Continued)

FOREIGN PATENT DOCUMENTS

AU    2007201613    5/2007

OTHER PUBLICATIONS

PCT Partial Search Report, dated Feb. 1, 2018 for International Application No. PCT/US2017/059429, 2 pages.
(Continued)

*Primary Examiner* — David P Porta
*Assistant Examiner* — Fani Boosalis

(57) ABSTRACT

Apparatus having an x-ray source and a DR detector configured to travel cooperatively around a radiographic imaging axis. An imaging volume defines a spatial region to be imaged by the x-ray source and the DR detector. Radiopaque fiducials are selectively positioned in the imaging volume.

17 Claims, 15 Drawing Sheets

(51) Int. Cl.
  *A61B 6/03*    (2006.01)
  *A61B 6/14*    (2006.01)
  *G06T 11/00*   (2006.01)
  *A61B 6/04*    (2006.01)

(52) U.S. Cl.
  CPC .............. *A61B 6/583* (2013.01); *A61B 6/587* (2013.01); *A61B 6/588* (2013.01); *A61B 90/39* (2016.02); *G06T 11/005* (2013.01); *A61B 2090/3966* (2016.02)

(56) References Cited

U.S. PATENT DOCUMENTS

| | | | |
|---|---|---|---|
| 9,717,467 B2 * | 8/2017 | Litzenberger | A61B 6/035 |
| 2008/0064952 A1 | 3/2008 | Li et al. | |
| 2011/0004431 A1 | 1/2011 | Ringholz et al. | |
| 2014/0199650 A1 * | 7/2014 | Moffson | B65D 83/00 433/27 |
| 2014/0350387 A1 * | 11/2014 | Siewerdsen | A61G 13/04 600/424 |
| 2015/0173703 A1 | 6/2015 | Siewerdsen et al. | |
| 2015/0204989 A1 | 7/2015 | Ni et al. | |
| 2017/0296137 A1 | 10/2017 | West et al. | |

OTHER PUBLICATIONS

International Search Report, dated Apr. 13, 2018 for International Application No. PCT/US2017/059429, 3 pages.

\* cited by examiner

GEOMETRIC CALIBRATION IN A CONE BEAM COMPUTED TOMOGRAPHY SYSTEM

CROSS REFERENCE TO RELATED APPLICATIONS

This application claims the benefit of and is a U.S. National Phase filing of PCT Application PCT/US2017/059429 filed Nov. 1, 2017 entitled "GEOMETRIC CALIBRATION IN A CONE BEAM COMPUTED TOMOGRAPHY SYSTEM", in the name of Michael C. Lalena, which claims benefit of U.S. Patent Application Ser. No. 62/416,178, filed Nov. 2, 2016, in the name of Michael C. Lalena, and entitled GEOMETRIC CALIBRATION IN A CONE BEAM CT SYSTEM.

BACKGROUND OF THE INVENTION

The subject matter disclosed herein relates to the field of volume imaging and more particularly to apparatus and methods that support geometric calibration of a cone beam computed tomography (CBCT) system.

Small-scale portable CBCT imaging systems provide useful tools to acquire volume image data for clinical use at locations other than conventional radiography facilities. Portable CBCT systems may be readily transported from site to site and quickly set up for capturing a sequence of images of a limb or other extremity of a patient, for example. The patient may be positioned within the system's imaging region during the imaging cycle, wherein the x-ray source and detector orbit the patient extremity to acquire a number of 2-D projection images of the extremity at a range of imaging angles.

FIGS. 1-4 illustrate one type of portable CBCT imaging system 100 that may be used for imaging a knee, elbow, or other extremity of a patient by allowing the patient extremity to be positioned within the system's imaging region, which region may be referred to herein as an imaging bore 114. The imaging system 100 may be rolled, either manually or under motor power, from place to place along a floor of a patient care facility. The central imaging bore 114 of the CBCT imaging system 100 is defined by an imaging apparatus 116. The imaging apparatus 116 may include a rounded housing 112, and a movable cover 118 that extends from one side of the imaging apparatus 116 to enclose a source or detector of the imaging system 100 as it travels around the imaging bore 114, as described herein in more detail subsequently. The imaging apparatus 116 may be configured to travel vertically, as indicated by the arrow 117, by a motorized rotatable vertical transport mechanism 121 that secures the imaging apparatus 116 to support column 128 via forked support arm 122. The imaging apparatus 116 may also be configured to rotate about axis 120 by rotating the rotatable vertical transport mechanism 121 (FIG. 4) and forked support arm 122. The imaging apparatus 116 may also be configured to rotate about an axis 119 through its connection points to forked support arm 122.

By way of example, FIG. 2 shows a patient 212 in a vertical position with one leg placed in the imaging bore 114 of the imaging apparatus 116 while the movable cover 118 extends from one end to another end of the imaging apparatus 116. The patient 212 is in position to radiographically image portions of one leg using the CBCT imaging system 100. In another example, FIG. 3 shows patient 212 in position to radiographically image a non weight-bearing ankle placed in the imaging bore 114 of the imaging apparatus 116. Image processing and display may be provided by a computer 140 or other processing system using an associated display 142.

Referring to FIG. 4, for a CBCT imaging exam using the imaging apparatus 116, the x-ray source assembly 422 and the detector 424 (receptor) inside the imaging apparatus 116 can make a full 360° sweep about imaging axis IA, capturing 2-D projection images at successive angles around a subject positioned in the imaging bore 114. The x-ray source assembly 422 and the detector 424 revolve about, or orbit, the imaging axis IA inside the imaging apparatus 116 supported by a circular or C-shaped support structure, or turntable, 416. Some system architectures may be limited in the rotational range of the source and detector to somewhat less than 360 degrees.

FIG. 4 illustrates internal imaging components of a portable CBCT system 100 similar to those illustrated in the imaging arrangements of FIGS. 1-3. The x-ray source assembly 422 and digital radiographic detector 424 may be coupled onto the support structure 416 for cooperative orbiting around the central imaging bore 114 which coincides with the imaging axis IA. A column 128 includes the rotatable vertical transport mechanism 121 for adjusting the height of imaging apparatus 116 and its components, which may be rotated about axes 119 and 120 to a suitable position for extremity imaging. Multiple x-ray sources may be used in x-ray source assembly 422 for directing radiation toward the imaging bore 114 and the detector 424.

FIG. 5 shows an alternate type of CBCT system 500 that is used for imaging the head and dental features of a standing patient 512. A source 522 and detector 524 revolve on a mount 550 about imaging axis IA and around the head of the patient 512 to capture multiple radiographic images thereof at a number of suitable angles for use in a volume image reconstruction procedure. A bite element 534, configured to be positioned in a mouth of a patient, may be used to assist in properly positioning the head of the patient 512 relative to the CBCT system 500. Alternatively, a chin rest or other receiving device configured to make contact with a portion of the head of a patient may be used to assist in properly positioning the head of the patient 512 relative to the CBCT system 500. Such a bite elements or a receiving device may be formed from a radiolucent material and fabricated to contain fiducials embedded therein.

In general, the algorithms used to reconstruct 3-D images from a number of captured 2-D radiographic projection images assume that the x-ray source is perpendicular to and centered, relative to the detector, at a given distance for every projection image in the exposure sequence. In practice, some algorithmic correction is used when a one-dimensional or two-dimensional array of x-ray sources is used, with one or more of the arrayed sources offset from a centered perpendicular axis relative to the detector. The reconstruction algorithms also generally assume that the radiographic imaging assembly does not move or shift, e.g., due to varying weight distribution, relative to the subject during an exposure sequence.

In day-to-day operation, however, the imaging apparatus may not maintain perfect geometrical alignment and other positional relationships between the various imaging components during a rotational imaging sequence. Due to factors such as jostling when being transported, configuration differences, and uneven weight distribution with rotational movement, precise geometric registration of the cooperating imaging components and their relative movement to each imaging position may not always be possible. Geometric calibration, initially performed when the system is first installed and periodically updated on-site, can be poorly suited to the task of maintaining proper positional accuracy. As the imaging system is used and moved from place to place, error and misregistration can make it difficult to reconstruct volume radiographic image data with sufficient accuracy for diagnostic use.

It can be costly and time-consuming to carry out periodic geometric calibration procedures regularly to compensate for errors resulting from normal movement, uneven weight distribution, gravity, and other sources. Thus, it would be useful to provide built-in tools for continuous geometric calibration of CBCT imaging systems during system use.

The discussion above is merely provided for general background information and is not intended to be used as an aid in determining the scope of the claimed subject matter.

BRIEF DESCRIPTION OF THE INVENTION

Disclosed is an apparatus having an x-ray source and a DR detector configured to travel cooperatively around a radiographic imaging axis. An imaging volume defines a spatial region to be imaged by the x-ray source and the DR detector. Radiopaque fiducials are selectively positioned in the imaging volume. An advantage that may be realized in the practice of some disclosed embodiments of the apparatus is improved calibration of the apparatus due to time and location proximity of the calibration procedure relative to patient imaging. An object of the present disclosure is to advance the art of volume radiographic imaging, particularly for portable imaging systems that can be moved from site to site. An embodiment of the present invention provides calibration tools integral to a CBCT apparatus, allowing ongoing geometric calibration of imaging system components.

In one embodiment an apparatus comprises a housing having an opening through the housing around an imaging axis. An x-ray source and a DR detector are configured to travel cooperatively within the housing around the imaging axis. An imaging volume extends radially from the imaging axis to define a region to be radiographically imaged by the x-ray source and the DR detector. A man-made radiopaque fiducial is selectively disposed in the imaging volume.

In one embodiment an apparatus comprises an x-ray source and a DR detector configured to travel cooperatively around a radiographic imaging axis. An imaging volume coincides with the imaging axis and extends radially therefrom. The imaging volume defines a region in space to be imaged by the x-ray source and the DR detector. A receiving element in the imaging volume receives and contacts a portion of a head of a patient. A man-made radiopaque fiducial is selectively positioned in the receiving element.

In one embodiment, a computer implemented method comprises acquiring a plurality of radiological projection images of a subject using a DR detector at a unique, corresponding acquisition angle. Each of the acquired projection images is processed by identifying one or more fiducials within contents of the acquired image and registering the contents of the acquired image according to the one or more identified fiducials. A volume image is reconstructed according to the processed acquired projection images, including modifying fiducial image data captured by pixels of the DR detector.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE EMBODIMENTS

This application claims priority to U.S. Patent Application Ser. No. 62/416,178, filed Nov. 2, 2016, in the name of Lalena, and entitled GEOMETRIC CALIBRATION IN A CONE BEAM CT SYSTEM, which is hereby incorporated by reference herein in its entirety.

In the context of the present disclosure, the term "code value" refers to the value that is associated with each 2-D image pixel or, correspondingly, each volume image data element or voxel in the reconstructed 3-D volume image. The code values for computed tomography (CT) or cone-beam computed tomography (CBCT) images are often, but not always, expressed in Hounsfield units that provide information on the attenuation coefficient of each voxel.

Two different types of calibration procedures are used to maintain CBCT system calibration for imaging quality:

(i) quantitative calibration, for measuring and calibrating system response according to Hounsfield values that relate to radiation density. This is the type of calibration taught, for example, in US Patent Application Publication US 2015/0173703 A1 by Siewerdsen et al. using calibration phantoms, which publication is hereby incorporated by reference as if fully set forth herein in its entirety; and (ii) geometric calibration that maintains pixel-by-pixel registration for each acquired image and compensates for mechanical drift and position shifting due to weight, movement, and other factors.

Embodiments of the present disclosure are directed to apparatuses, systems and methods for geometric calibration (ii), providing solutions that can be particularly useful with portable CBCT systems.

Figure 6:
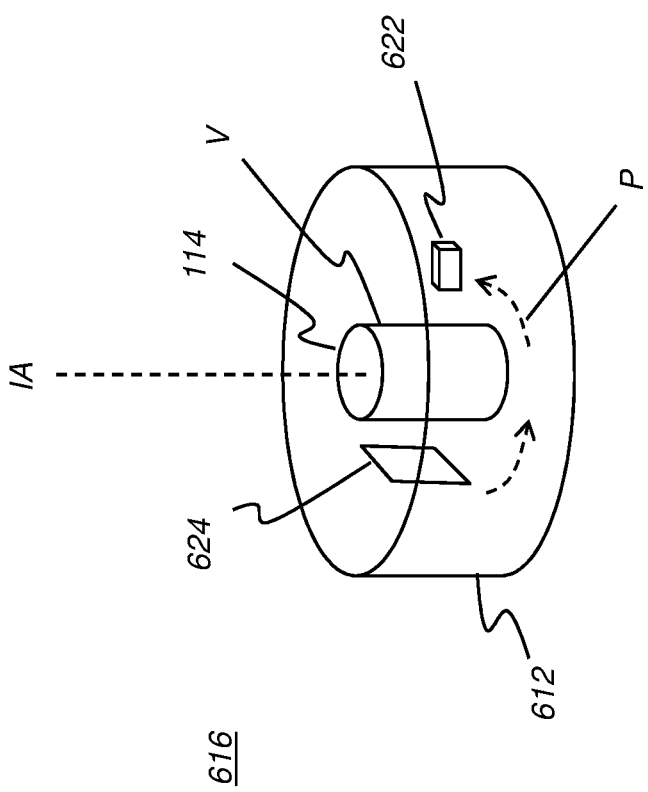
FIG. 6 is a schematic diagram of spatial relationships between imaging and support components of an exemplary CBCT imaging system.

Embodiments disclosed herein support geometric calibration of a CBCT system configured such that the x-ray source and detector are cooperatively coupled together or otherwise configured to move synchronously about a subject positioned within an imaging volume, which subject position should preferably coincide with an imaging axis formed by the orbital movement of the x-ray source and detector. Referring to the schematic diagram of FIG. 6, relationships of CBCT imaging system 616 components and support structures are shown. A housing 612 encloses an x-ray source 622 and a digital radiography (DR) detector 624 that are mechanically coupled or otherwise configured to travel cooperatively and synchronously within housing 612 along an orbital travel path P about an imaging axis IA. In one embodiment, the exterior of the housing 612 is shaped as a cylinder and the x-ray source 622 and the digital radiography (DR) detector 624 are configured to travel along a portion or along an entirety of a circular path P within the cylindrical housing 612 while remaining diametrically opposed in relation to the imaging axis IA. An imaging bore 114 is formed by a cylindrical opening in the cylindrical housing 612. In the embodiment of FIG. 6, a central axis of the imaging bore 114 coincides with imaging axis IA and may be generally symmetrical about the imaging axis IA, having imaging bore 114 sidewalls facing the imaging axis IA. The cylindrical imaging volume V generally defines the spatial region to be imaged by the x-ray source 622 and the DR detector 624. Imaging volume V and imaging bore 114 may have substantially the same radial dimension, however, the imaging volume V may be configured to have a lesser or greater radius than the imaging bore 114. In one embodiment, the imaging volume V may be increased by increasing a distance between the x-ray source 622 and the DR detector 624. Conversely, the imaging volume V may be decreased by decreasing a distance between the x-ray source 622 and the DR detector 624. In one embodiment, the imaging volume V may be increased and decreased by increasing and decreasing the size of a collimator aperture at the x-ray source 622, thereby modifying a size of a cross section of the x-ray beam emitted by the x-ray source 622. In one embodiment, one or more portions of the imaging bore 114, e.g., movable sidewalls or other portion described herein, rotate synchronously with x-ray source 622 and detector 624. Fiducials, as described herein, may be positioned on moving or stationary portions of the imaging bore 114 or proximate the imaging bore 114 during radiographic imaging. The positioned fiducials may be directly visible to the operator, before, during or after radiographic imaging, or they may not be visible, due to being embedded within or behind a surface or secured in an opaque container.

In one embodiment, a mechanism for geometric calibration of the CBCT imaging system uses an arrangement of man-made fiducials that are included as integral components of the CBCT system itself. If the fiducials are disposed in or near the imaging volume V, they would appear within each captured projection image. Because the position of the fiducials within radiographic images can be positively identified with high accuracy, either under programmed image analysis or by human observation, the relative clarity and intensity of fiducials in a radiographic image makes the fiducials unambiguous. The fiducials may, therefore, be used to provide geometric calibration with each captured radiographic image, and so may be readily identified and digitally removed from the captured image content for 3-D image reconstruction.

Figure 8:
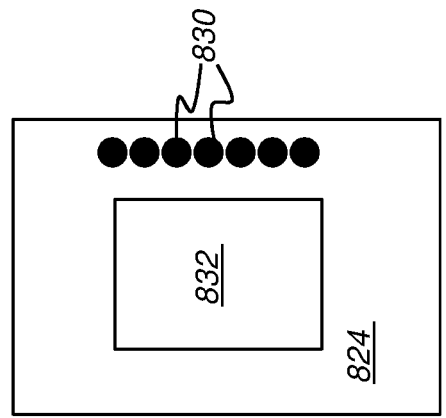
FIG. 8 is a schematic diagram of an exemplary radiographic image with imaged fiducials along an edge of the image.
Figure 7:
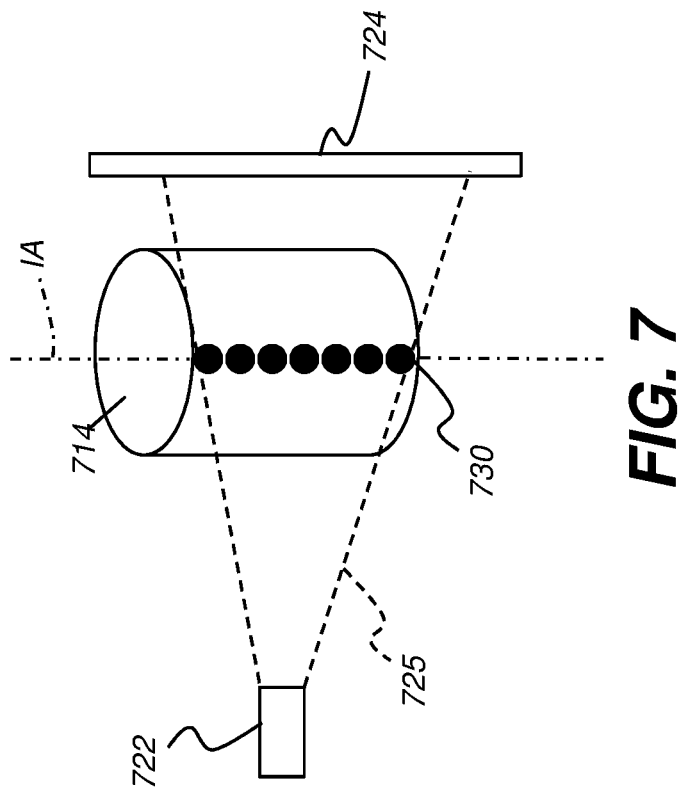
FIG. 7 is a schematic diagram of an exemplary imaging bore and a column of fiducials.
Figure 10:
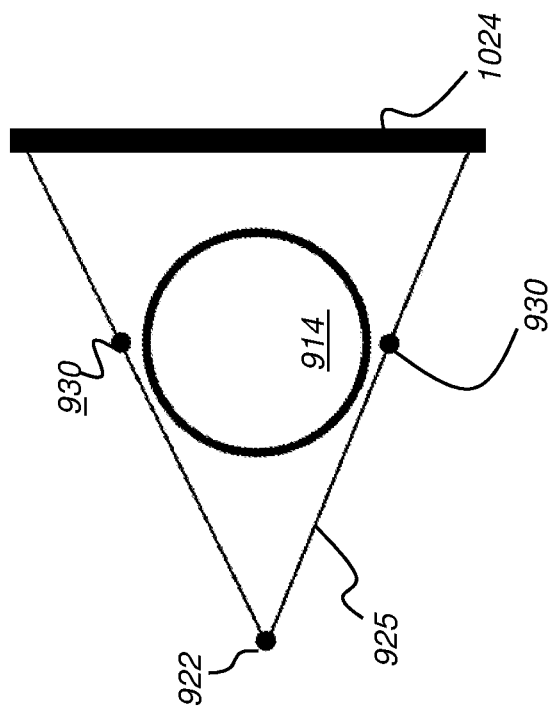
FIG. 10 is a schematic diagram of another exemplary imaging apparatus with fiducials proximate sides of the imaging bore.
Figure 9:
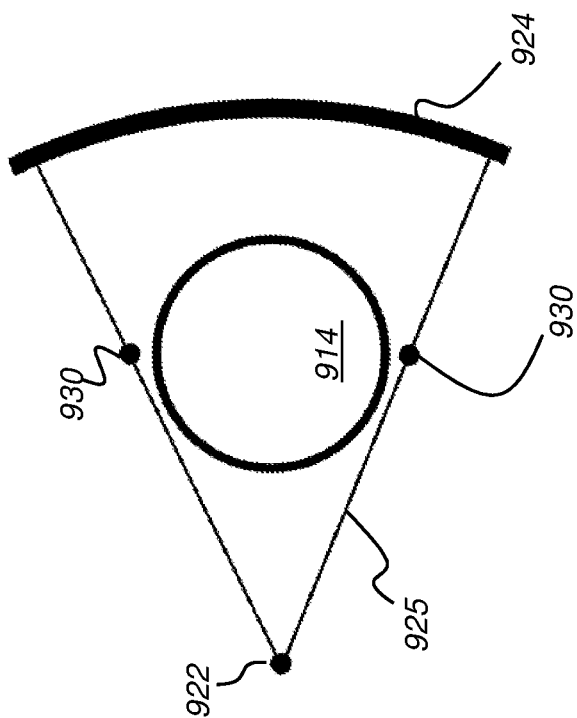
FIG. 9 is a schematic diagram of an exemplary imaging apparatus with fiducials proximate sides of the imaging bore.

Referring to the schematic views of FIG. 7, one arrangement of exemplary fiducials 730 uses one or more columns of fiducials 730 arranged along a sidewall of cylindrical imaging bore 714 or, alternately considered, along the side walls of an imaging volume V. As shown in FIG. 7, the x-ray source 722 and detector 724 are arranged to capture an image volume less than the volume V of the imaging bore 714, with respect to the emitted x-ray beam 725 passing through less than the total height dimension of the imaging bore 714. The schematic view of FIG. 8 shows a radiographic image 824 of fiducials 830 captured along an edge of the radiographic image 824. FIGS. 9 and 10 are top views of the arrangement of FIG. 7, using a curved detector 924 and a flat panel detector 1024, respectively, and illustrating placement of fiducials 930 in a columnar arrangement proximate the side walls of imaging bore 914. In the examples of FIGS. 9 and 10, the x-ray source 922 and detector 924, 1024, respectively, are arranged to capture more than the entire volume of the imaging bore 914 with respect to the emitted x-ray beam 925 passing through more than the total diameter dimension thereof.

Referring back to FIG. 8, the imaging of fiducials 730 by placing them proximate the side walls of the imaging volume 714, i.e., along the periphery of the DR image 824, keeps the imaged fiducials 830 away from a central portion 832 of the acquired DR image 824. The central image portion 832, which generally contains image content that is of most diagnostic interest, may be considered as a centered rectangular image portion that is nominally about half the height and half the width of the captured DR image 824. In one embodiment, disclosed CBCT systems may be designed to capture fiducial images 830 near edges of the DR images 824, away from a central portion 832 thereof. During image processing, the image location of the fiducials 830 may be readily digitally ascertained under program control and the image pixels containing fiducial image data may be digitally processed to correct or eliminate fiducial image data from a 2-D or 3-D reconstruction algorithm. As shown in FIGS. 9 and 10, fiducials 930 may be positioned just outside the image bore 914, such as by using a support structure within the imaging apparatus 616 housing 612. These fiducials may be selectively fixed in position or may be configured electromechanically to travel simultaneously with the source 922 and detector 924, 1024.

Figure 11:
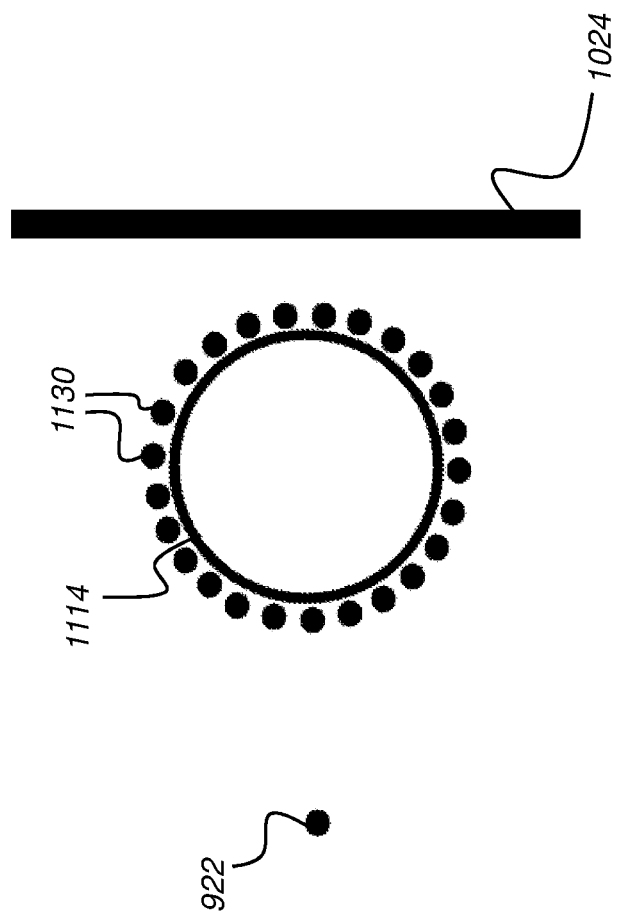
FIG. 11 is a schematic diagram of another exemplary imaging apparatus with fiducials proximate sides of the imaging bore.
Figure 12:
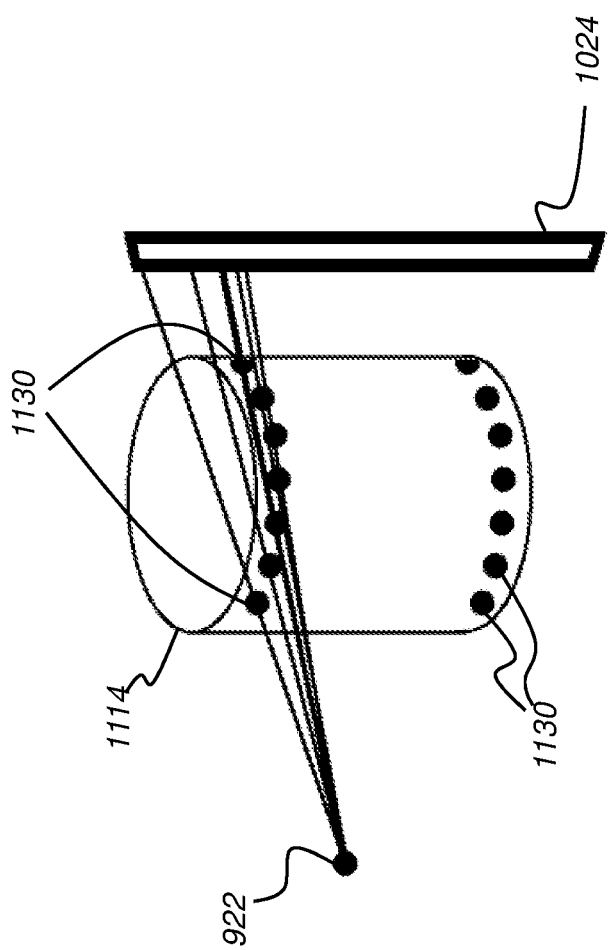
FIG. 12 is a schematic diagram of an another exemplary imaging apparatus with fiducials proximate sides of the imaging bore.
Figure 13:
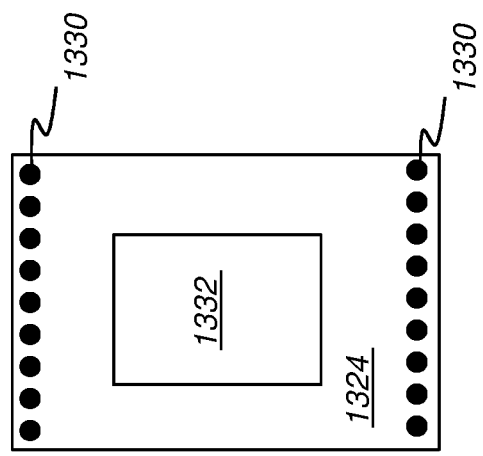
FIG. 13 is a schematic diagram of an exemplary radiographic image with imaged fiducials along the top and bottom edges of the image.

The schematic top view diagram of FIG. 11 shows fiducial assemblies 1130 arranged in a pattern about the imaging bore 1114 using one or more fiducial assemblies 1130 near the top and bottom edges of the imaging bore 1114. The schematic perspective view diagram of FIG. 12 shows the fiducial assemblies 1130 arranged in a pattern about the imaging bore 1114 using one or more fiducial assemblies 1130 near the top and bottom edges of the imaging bore 1114. FIG. 13 is a schematic diagram of an exemplary digital radiographic image 1324 with imaged fiducials 1330 along the top and bottom edges of the DR image 1324. Similar to the columnar arrangement of fiducials 730 and imaged fiducials 830, shown in FIGS. 7-8, imaged fiducials 1330 are positioned peripherally with respect to the central portion 1332 of the DR image 1324. To minimize processing time for digitally correcting and/or removing imaged fiducials 1330, the fiducials 1130 may be selectively placed, relative to an imaging bore, to appear in an unused or negligible portion of a DR image 1324, which is typically near the periphery or border of the DR image 1324.

Figure 14:
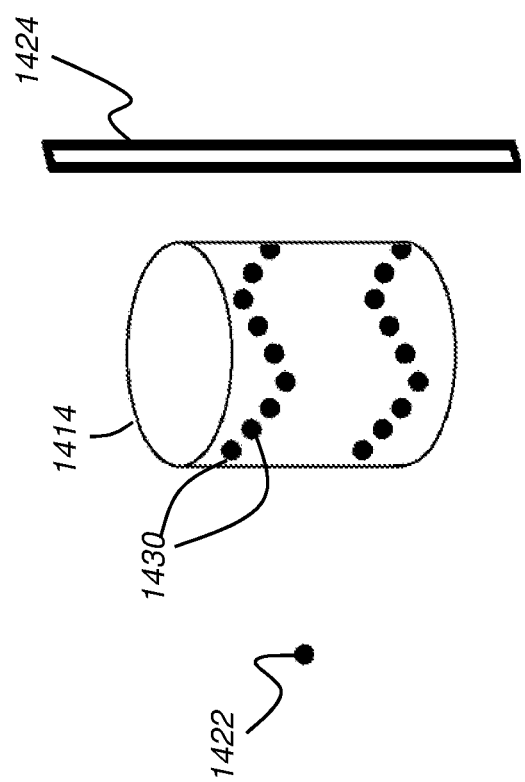
FIG. 14 is a schematic diagram of fiducials arranged in a sinusoidal pattern about an imaging bore using a removable holder.
Figure 15:
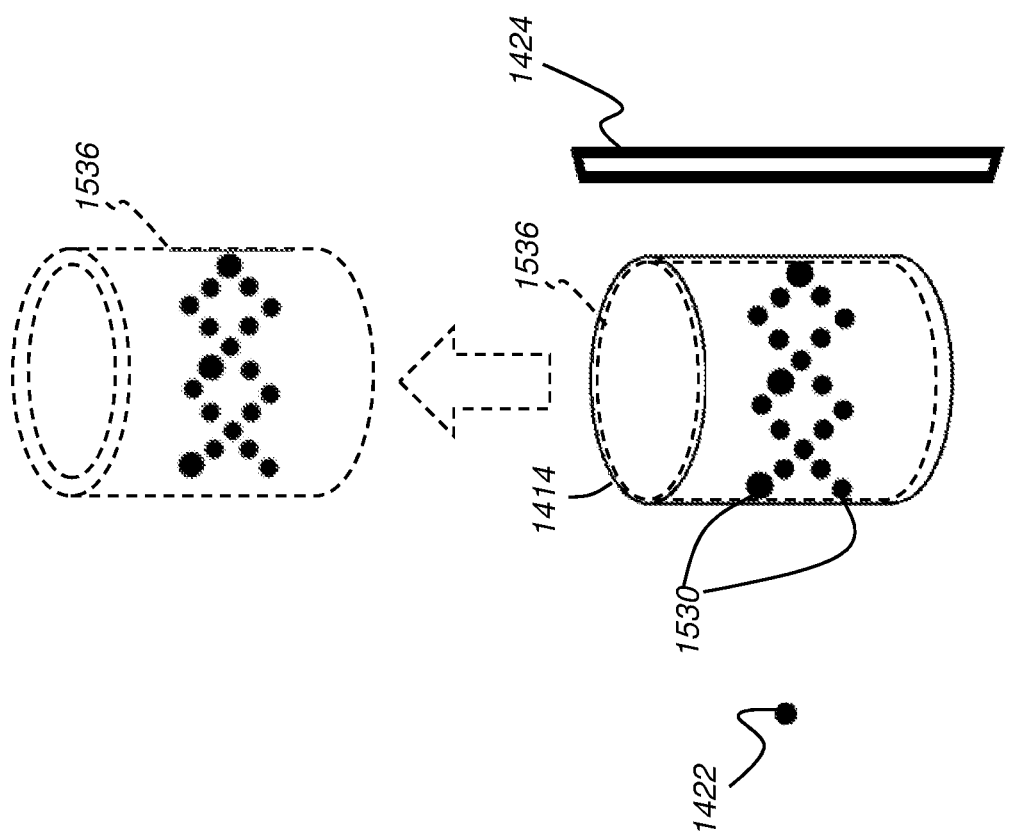
FIG. 15 is a schematic diagram of fiducials arranged in two sinusoidal patterns about an imaging bore.

In addition to curved, circular or linear (columnar) patterns, fiducials may be arranged in a variety of patterns. The side view schematic diagram of FIG. 14 illustrates a sinusoidal pattern of fiducials 1430 positioned proximate side walls of an imaging bore 1414 between an x-ray source 1422 and a DR detector 1424. Similarly, the side view schematic diagram of FIG. 15 illustrates a double sinusoidal intersecting pattern of fiducials 1530 similarly positioned. Random arrangements of fiducials may also be used. The fiducials may be positioned in any suitable location, including mounted on the outside or inside of an imaging bore using structures integrally formed with imaging apparatus 116, 616, embedded within the material that forms the side walls of the imaging bore, or affixed to a stationary or movable imaging assembly, mounted on a door that encloses the bore, mounted on the housing, or mounted on the patient or on an optional holder that secures fiducials against the patient, such as a flexible strap having pockets to hold fiducials secured to a patient extremity, which is held in a fixed position proximate the patient when the patient is in position for imaging. As disclosed herein, the fiducials are illustrated in the shape of spheres made of a radiopaque material. Spherical fiducials may be preferred because of their symmetry in a variety of imaging angles. Such symmetry may provide an advantage during image processing such as during digital correction or removal of fiducial image data. Alternately, fiducials of some other shape may be used.

FIG. 15 illustrates a removable cylinder 1536, shown in dashed line, having a selected thickness and fabricated from a radiolucent material, whereto fiducials 1530 may be attached, or embedded within. Radiolucent cylinder 1536 with fiducials 1530 may be configured to be manually insertable, or attachable and detachable, into an imaging bore 1414 of a CBCT imaging system. The radiolucent cylinder 1536 may be precisely registered into position within an imaging bore 1414 during a geometric calibration procedure, then may be manually detached (removed) from the imaging bore to begin radiographic imaging of a patient without the fiducials 1530 present. Alternatively, the removable radiolucent cylinder 1536 with fiducials 1530 may remain in place during radiographic imaging.

Figure 16:
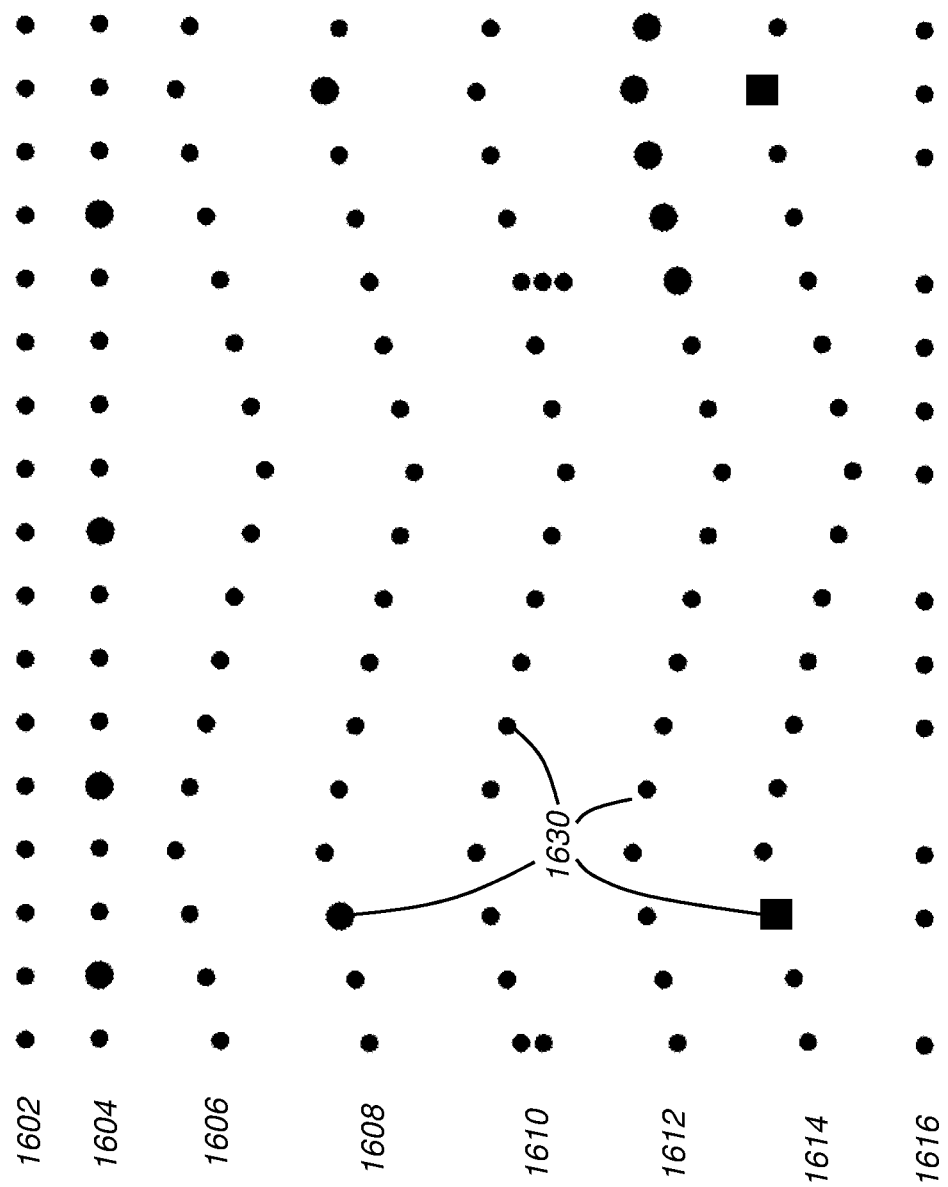
FIG. 16 is a diagram of different exemplary patterns of fiducials.

As described herein, the fiducials may be of different sizes, shapes, and materials, which can ease identification in some cases. FIG. 16 is a diagram of different exemplary patterns of fiducials 1630 that may be arranged proximate to or within an imaging bore in any manner disclosed herein. Some of the possible variations include linear patterns 1602; curved patterns, such as sine wave patterns 1606; stepped patterns; circular patterns; varying sizes 1604, 1608, 1612; varying shapes 1614; periodic pattern 1616; grouped patterns 1610; scaled sizing to show gradual increase or decrease; and sparse distribution patterns, for example. Some of fiducials 1630 may be at least twice as large as others in terms of volume or radius. Fiducials 1630 of different shapes, such as spherical and cube-shaped fiducial patterns 1614, can be used to help register image content obtained at different rotational angles.

The fiducials disclosed herein may be formed of lead or other radiopaque materials. They may be embedded within or affixed to the side wall of the imaging bore. Some or all of the fiducials may include other materials, including materials of varying density and opacity, such as plastics, ceramics, or composite materials.

Figure 1:
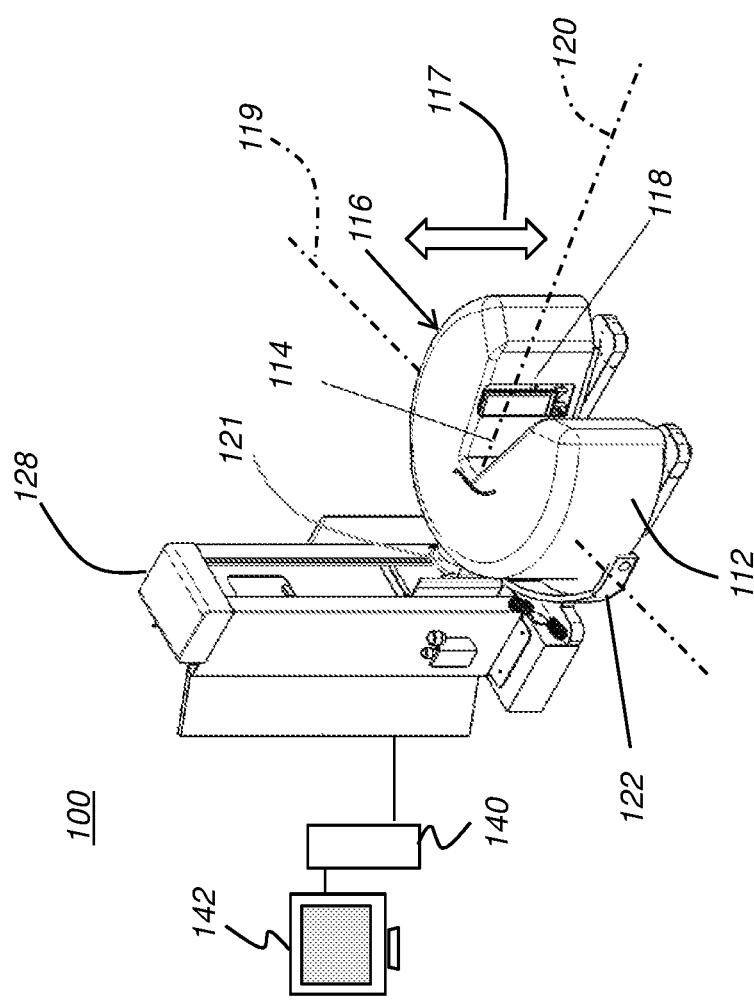
FIG. 1 is a perspective view of an exemplary portable CBCT imaging system used for imaging an extremity of a patient.
Figure 2:
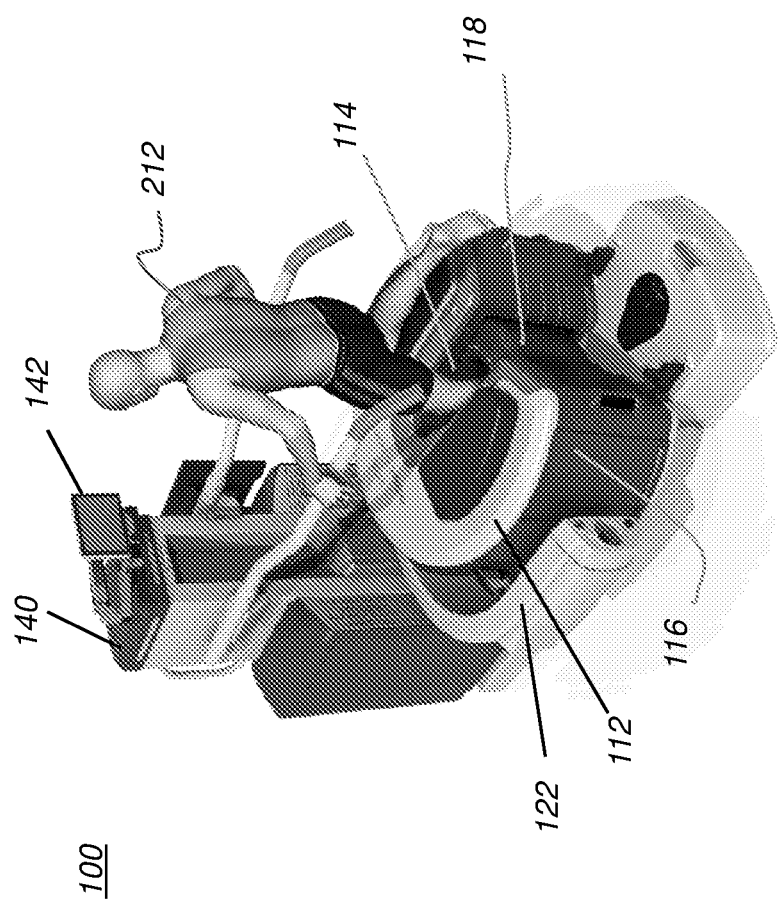
FIG. 2 is a perspective view of an exemplary portable CBCT imaging system used for imaging of an extremity of a patient.
Figure 3:
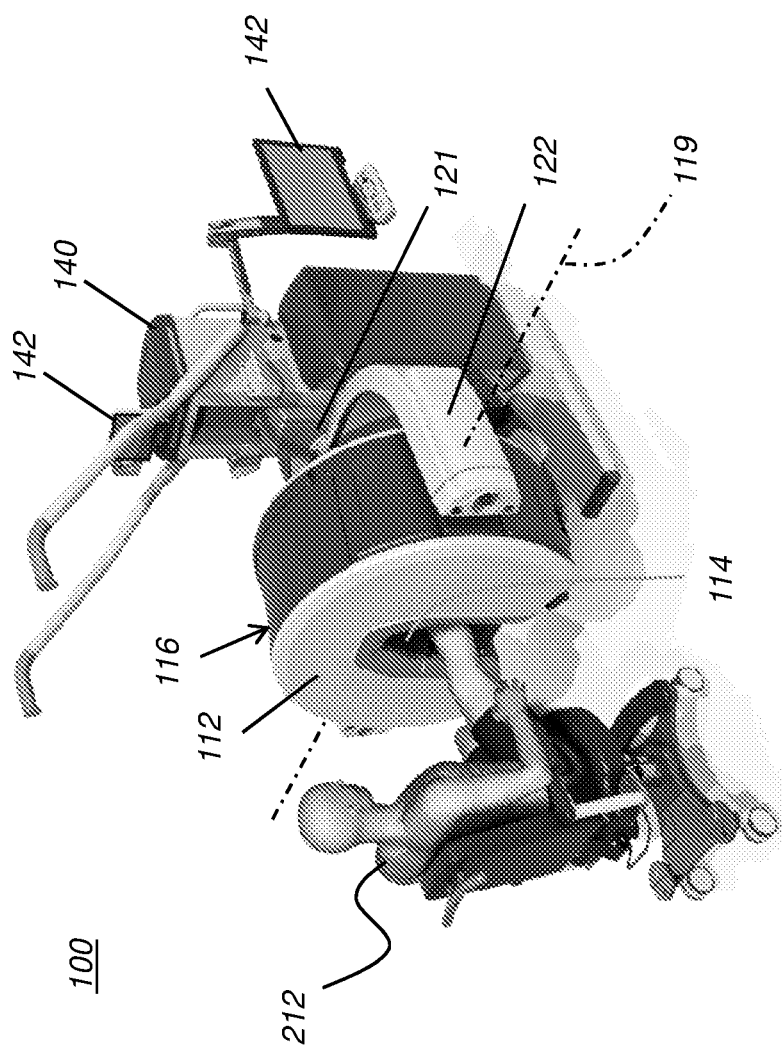
FIG. 3 is a perspective view of an exemplary portable CBCT imaging system used for imaging an extremity of a patient.
Figure 4:
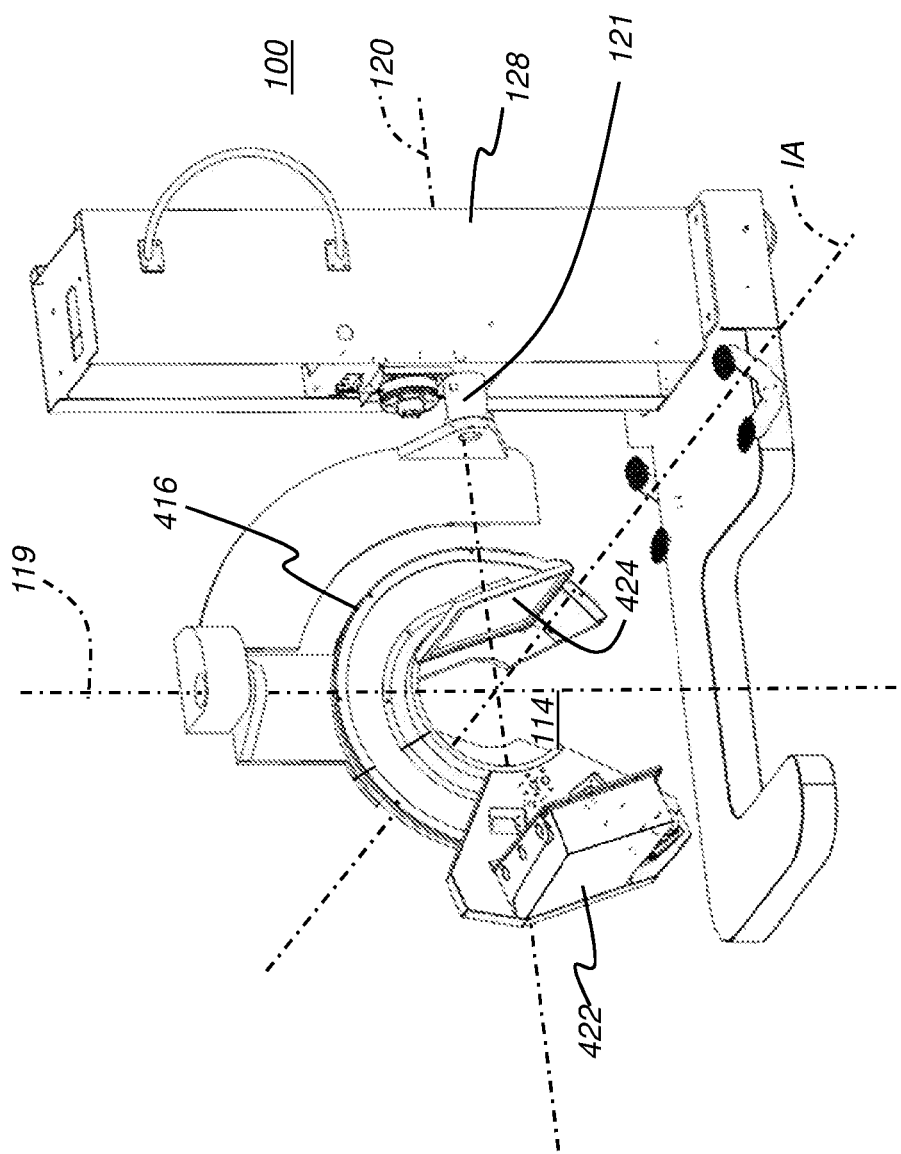
FIG. 4 is a perspective view of internal components of an exemplary portable CBCT imaging system used for imaging of an extremity of a patient.
Figure 5:
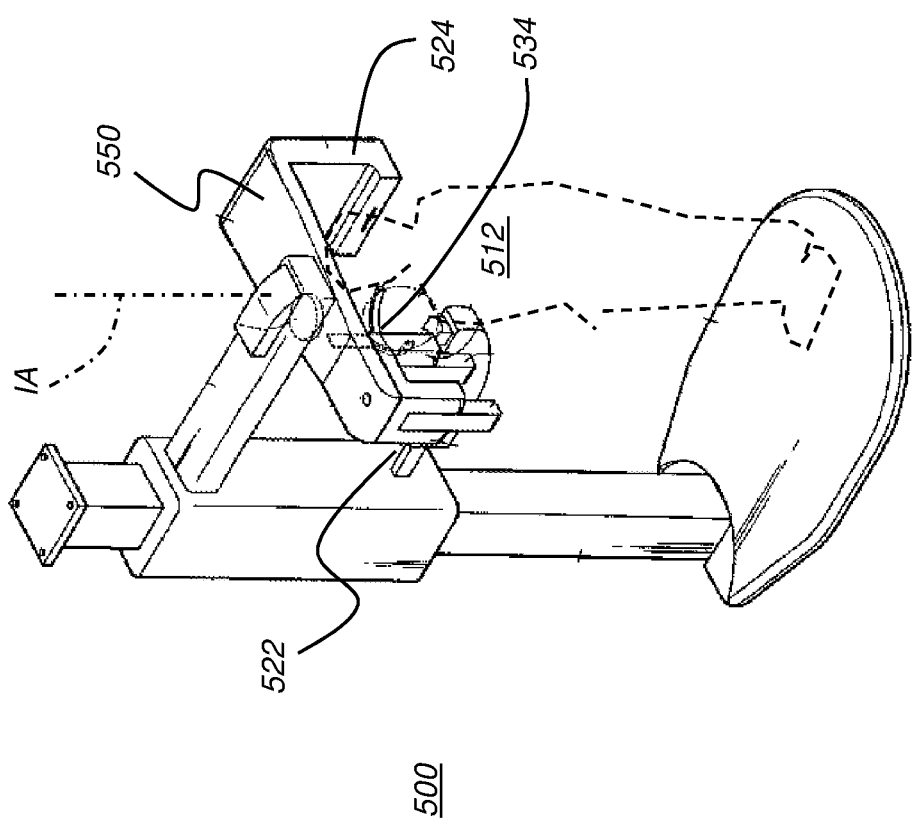
FIG. 5 is a perspective view of another exemplary portable CBCT imaging system used for imaging the head of a patient.

In one embodiment, for example, in the patient head imaging apparatus of FIG. 5, no bore is available to position fiducials. In this embodiment, patient-supporting devices that have a known geometric relationship to scanning components, such as the bite element 534, or other patient head receiving element disclosed herein, may include associated fiducials attached to or embedded therein. Alternately, fiducials may be mounted at one or more suitable positions along the rotating arm that travels simultaneously with the source and detector.

During a computed tomography (CT) or CBCT imaging exam, the x-ray source 122 and detector 124 sweep over a broad angular range and, in some cases, may even make a full 360 degree sweep, acquiring a set of multiple 2-D projection images, each image having a corresponding angle with respect to the image volume. The algorithms that reconstruct the 3-D images may compensate for some geometric variation, since, for each 2-D projection image acquired, the x-ray source may not be exactly perpendicular to the detector and centered at a precise distance with respect to the detector. Some reconstruction algorithms may assume that the circular path of source and detector remain within the same plane throughout the orbital scan cycle. However, programmed algorithm adjustments may be made to the data to compensate for some amount of predicted or measured skew. Fiducials of the disclosed embodiments may be used by position-sensing algorithms to verify or correct image data position, skew, or offset for each individual 2-D projection image in the acquired image data set. Fiducials may also be used in combination with inclinometers and other sensors within an imaging apparatus for verifying geometric position of source and detector.

As each projection image is acquired, the imaged x-ray opaque fiducials form part of the captured radiographic image content. The pixel-by-pixel locations of the captured digital fiducial images are obtained and compared against a target value for accurate geometric calibration. A slight shift of the exposure data may be readily detected, to at least 1.0 pixel resolution, and used to adjust registration of the corresponding projection image to the needed geometry for reconstruction purposes.

Pixels associated with a fiducial may be digitally removed from the projection image data prior to the reconstruction procedure with little or no perceptible impact on diagnostic image quality, since x-rays from numerous imaging angles are typically sufficient for accurately characterizing the underlying anatomy. Image pixels that are blocked by a fiducial may be logically ignored by the reconstruction algorithm. As an alternative, conventional in-painting or interpolation processing could be used in order to remove pixels associated with a fiducial.

Using an embodiment of the present disclosure, geometric calibration is straightforward and may be readily performed, including performed separately, such as immediately after the system is transported to a patient care facility, without a patient or other imaging subject in position. No external phantom device is needed.

Figure 17:
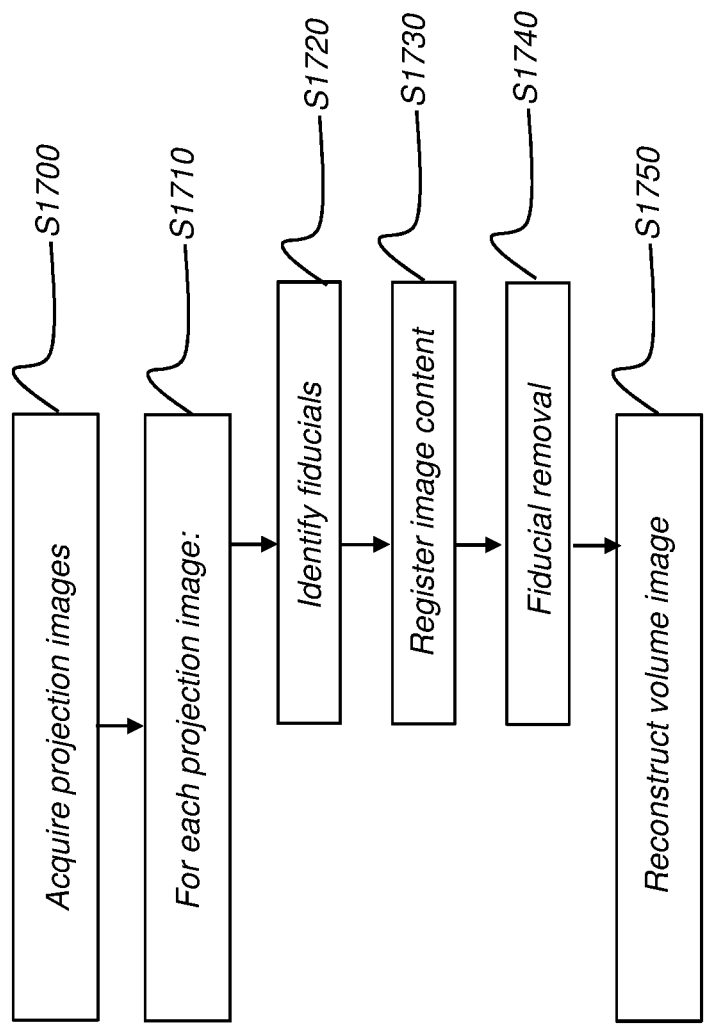
FIG. 17 is a flow diagram of a sequence for processing projection image content using fiducials.

The logic flow diagram of FIG. 17 shows a sequence for processing projection image content using fiducials according to an embodiment of the present disclosure. A set of projection images, each captured at a corresponding acquisition angle relative to the imaged patient, is obtained in an acquisition step S1700. A programmed subroutine S1710 executes steps S1720, S1730 and S1740 for each captured projection image. In fiducials identification step S1720, the fiducials in each projection image are identified according to pixel image data intensity and pixel location (i.e., row and column). Registration step S1730 adjusts the image content per pixel for the corresponding projection image according to the fiducial pixel location. A fiducial removal step S1740 then makes the necessary adjustments to pixel intensity data to compensate for fiducials in each of the captured projection images. Adjustments may include blocking out, or removing (e.g., zeroing a pixel value), portions of the projection image data that include fiducial content. This may include masking edges of one or more projection images or masking projection image pixels that contain fiducial image data. According to an alternate embodiment of the present disclosure, pixel replacement can be performed, using known in-painting or interpolation techniques in order to replace fiducial content in the projection image. A standard reconstruction procedure S1750 can then be performed, forming the volume reconstructed image for subsequent display and analysis.

Consistent with one embodiment, the present invention utilizes a computer program with stored instructions that control system functions for image acquisition and image data processing for image data that is stored and accessed from an electronic memory. As can be appreciated by those skilled in the image processing arts, a computer program of an embodiment of the present invention can be utilized by a suitable, general-purpose computer system, such as a personal computer or workstation that acts as an image processor, when provided with a suitable software program so that the processor operates to acquire, process, transmit, store, and display data as described herein. Many other types of computer systems architectures can be used to execute the computer program of the present invention, including an arrangement of networked processors, for example.

The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the image data processing arts will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of those in the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art.

Such other examples are intended to be within the scope of the claims if they have structural elements that do not differ from the literal language of the claims, or if they include equivalent structural elements with insubstantial differences from the literal language of the claims.

The invention claimed is:

1. Apparatus comprising:
a housing having an opening through the housing, the opening surrounding an imaging axis;
an x-ray source and a DR detector configured to travel cooperatively within the housing around the imaging axis;
an imaging volume extending radially from the imaging axis, the imaging volume defining a spatial region to be radiographically imaged by the x-ray source and the DR detector;
a plurality of man-made radiopaque fiducials selectively disposed in the imaging volume;
a patient to be radiographically imaged by the apparatus, the patient positioned in the imaging volume while the radiopaque fiducials remain in the imaging volume; and
a processing system configured to reconstruct a volume image of the patient, to calibrate reconstruction of the volume image of the patient using radiographic images of the patient and of the radiopaque fiducials appearing therein as captured by the DR detector, to digitally remove the radiopaque fiducials appearing in the radiographic images of the patient, and to reconstruct the volume image of the patient using the radiographic images of the patient having the radiopaque fiducials removed therefrom.

2. The apparatus of claim 1, wherein the radiopaque fiducials are each formed in a shape selected from the group consisting of spheres, rectangular prisms, prisms, cuboids, pyramids, cylinders, cones, and frustums.

3. The apparatus of claim 1, wherein the radiopaque fiducials are disposed in a sinusoidal pattern in the imaging volume such that each radiographic image captured by the DR detector includes the plurality of fiducials displayed in the sinusoidal pattern.

4. The apparatus of claim 1, wherein the radiopaque fiducials are fixed on a mechanism that travels simultaneously with the source and detector around the imaging axis.

5. The apparatus of claim 1, wherein the radiopaque fiducials are embedded in a material portion of the housing.

6. The apparatus of claim 1, wherein the radiopaque fiducials are made from lead (Pb).

7. The apparatus of claim 1, wherein the radiopaque fiducials are arranged in a pattern comprising a vertical line, horizontal line, a curve, a wave, a stepped formation, a circle, or other geometric shape.

8. The apparatus of claim 1, wherein one of the radiopaque fiducials differs from remaining ones of the radiopaque fiducials by size, position, pattern deviation, or material.

9. The apparatus of claim 1, wherein the processing system generates calibration data using the radiopaque fiducials.

10. The apparatus of claim 1, wherein the radiopaque fiducials are selectively disposed such that they appear proximate an edge of a radiographic image captured by the DR detector.

11. A computer implemented method comprising:
acquiring a plurality of radiological projection images of a subject using a DR detector, including acquiring each of the projection images of the subject at a unique, corresponding acquisition angle;
processing each of the acquired projection images of the subject by:
(i) identifying one or more fiducials within the acquired image of the subject;
(ii) registering the contents of the acquired image of the subject using the one or more identified fiducials;
(iii) modifying the acquired projection images of the subject including digitally removing fiducial image data of the one or more identified fiducials from the acquired projection images of the subject; and
reconstructing a volume image of the subject using the processed and modified acquired projection images of the subject.

12. The method of claim 11, further comprising shaping the one or more fiducials as spheres, rectangular prisms, prisms, cuboids, pyramids, cylinders, cones, and frustums.

13. The method of claim 11, further comprising disposing a plurality of the fiducials in a sinusoidal pattern.

14. The method of claim 11, further comprising forming the fiducials from lead (Pb).

15. The method of claim 11, further comprising arranging the fiducials in a pattern comprising a vertical line, horizontal line, a curve, a wave, a stepped formation, a circle, or other geometric shape.

16. The method of claim 11, further comprising calibrating the step of reconstructing the volume image of the subject using the fiducials.

17. The method of claim 11, further comprising generating calibration data using the fiducials.

* * * * *